United States Patent [19]

Schmitt et al.

[11] 4,185,105

[45] Jan. 22, 1980

[54] 4-PHENYL-8-AMINO-TETRAHY-DROISOQUINOLINES AND ANTIDEPRESSANT USE

[75] Inventors: Karl Schmitt; Irmgard Hoffmann, both of Bad Soden am Taunus; Ulrich Schacht, Hofheim am Taunus, all of Fed. Rep. of Germany

[73] Assignee: Hoechst Aktiengesellschaft, Frankfurt, Fed. Rep. of Germany

[21] Appl. No.: 910,781

[22] Filed: May 30, 1978

[30] Foreign Application Priority Data

Jun. 1, 1977 [DE] Fed. Rep. of Germany ....... 2724610

[51] Int. Cl.² ..................... A61K 31/47; C07D 217/02
[52] U.S. Cl. ..................................... 424/258; 546/143
[58] Field of Search ..................... 424/258; 260/288 D

[56] References Cited

U.S. PATENT DOCUMENTS

| | | | |
|---|---|---|---|
| 3,384,640 | 5/1968 | Muchowski | 260/288 D |
| 3,577,424 | 5/1971 | Ehrhart et al. | 424/258 |

*Primary Examiner*—Stanley J. Friedman

*Attorney, Agent, or Firm*—Curtis, Morris & Safford

[57] ABSTRACT

4-Phenyl-8-amino-tetrahydroisoquinolines of the formula

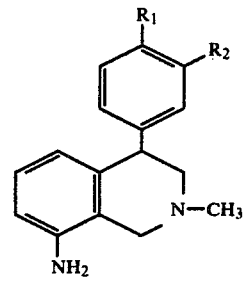

in which $R_1$ stands for bromine and $R_2$ stands for hydrogen or both $R_1$ and $R_2$ represent chlorine, and their salts with physiologically tolerated acids, pharmaceutical preparations prepared therefrom, process for the manufacture of these preparations and their use for the treatment of depressive conditions.

5 Claims, No Drawings

4-PHENYL-8-AMINO-TETRAHYDROISOQUINOLINES AND ANTIDEPRESSANT USE

4-Phenyl-8-amino-tetrahydroisoquinolines of the general formula

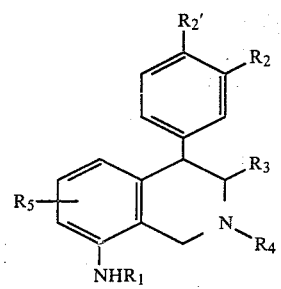

in which $R_1$ denotes hydrogen, a lower alkyl group or the benzyl group, $R_2$ denotes hydrogen, the methyl group, chlorine or fluorine atoms, $R_2'$ denotes hydrogen, methyl-, methoxy-, hydroxy groups or halogen atoms, $R_3$ and $R_4$ denote hydrogen or a lower alkyl group and $R_5$ denotes hydrogen, a chlorine atom or a methoxy group in the 5- or 6-position, are known from German Specification (Deutsche Offenlegungsschrift No. 1 795 829).

Now it has been found that two previously unknown compounds considerably surpass the known class of compounds of the above formula I in their antidepressive action.

Thus, the present selective invention relates to compounds of the formula II

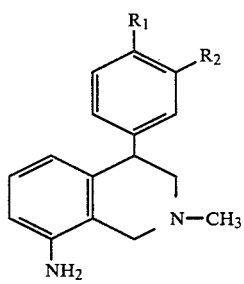

in which either $R_1$ represents bromine and $R_2$ represents hydrogen or both $R_1$ and $R_2$ represent chlorine.

The novel compounds of formula II are distinguished, inter alia, by an increased action in the inhibition test for the serotonin uptake over that of the known class of compounds. While the known compounds of formula I (with the exception of compounds of formula II) inhibit the uptake of serotonin only at a higher concentration, the compounds of formula II effect an inhibition of the serotonin uptake which could hitherto not have been achieved with the compounds of formula I.

The inhibition of the uptake of serotonin results in an increased antidepressant action and is, therefore, of considerable importance in the therapy. Therefore, the compounds of formula II are valuable pharmaceuticals which are used for the treatment of depressive conditions.

The compounds of formula II are prepared according to the process described in German Patent Specification No. 1 670 694 by cyclisation of the corresponding N-(2-aminobenzyl)-α-methylaminomethylbenzyl alcohols. The compounds of the formula II may form salts with one or two equivalents of an acid. With a view to their use as medicaments, physiologically tolerated acids are used for the salt formation. Inorganic acids are, for example: hydrohalic acids such as hydrochloric acid and hydrobromic acid as well as sulfuric acid, phosphoric acid and amidosulfonic acid. Organic acids are, for example: formic acid, acetic acid, propionic acid, lactic acid, glycolic acid, gluconic acid, maleic acid, succinic acid, tartaric acid, benzoic acid, salicylic acid, citric acid, aceturic acid or oxyethanesulfonic acid.

The following Examples illustrate the invention:

EXAMPLE 1

50 g of 3,4-dichloroacetophenone in 300 ml of methylene chloride are brominated with bromine at room temperature. The ω-bromo-3,4-dichloroacetophenone so obtained is directly used. First, the ω-bromo-compound is dissolved in 300 ml of ethanol. The solution of 42.6 g of N-methyl-2-nitrobenzylamine and 33.1 g of N-ethyl-N,N-diisopropylethylamine in 100 ml of ethanol is added dropwise at 60° C. The mixture is stirred for 1 hour at room temperature, then for 2 hours at the boiling temperature and finally evaporated to dryness. The residue is dissolved in water and ether; the latter is separated, dried with potassium carbonate and evaporated again.

The residue forms a salt with ethanol/hydrochloric acid and 19 g of N-(3,4-dichlorophenacyl)-N-methyl-2-nitrobenzylamine hydrochloride are obtained. Melting point 165° C. (decomposition).

From the hydrochloride, the base is again prepared with methylene chloride and is isolated in the form of an oil (18 g). Carbonyl and nitro groups are then hydrogenated successively. The carbonyl group yields with sodium borohydride (5 g in 50 ml of methanol to 18 g of acetophenone derivative in 250 ml of methanol) 15 g of the hydroxy compound, the nitro group is then hydrogenated with Raney nickel under normal pressure and room temperature. The uptake of hydrogen is as calculated; 14 g of N-2-aminobenzyl-α-N-methylaminomethyl-3,4-dichlorobenzyl alcohol in the form of an oily product are obtained.

14 g of the oil so obtained in 100 ml of methylene chloride are added dropwise, while stirring, at 5°–10° C., to 70 ml of sulfuric acid (conc.) for cyclisation. The mixture is stirred for 1 hour at room temperature and then poured onto crushed ice. Upon further cooling the mixture is neutralised with concentrated NaOH while further cooling, whereupon the reaction product precipitates in oily form. The base is isolated with methylene chloride and 8 g of the isoquinoline derivative as a base are obtained.

EXAMPLE 2

Starting from 4-bromoacetophenone, 8-amino-4-(4-bromophenyl)-2-methyl-1,2,3,4-tetrahydroisoquinoline-hydrogenomaleinate, melting at 189°–191° C., is obtained according to the method described in Example 1.

We claim:
1. A 4-phenyl-8-amino-tetrahydroisoquinoline of the formula

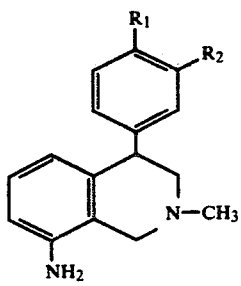

and a salt thereof with a physiologically tolerated acid, wherein $R_1$ is bromine and $R_2$ is hydrogen or both $R_1$ and $R_2$ are chlorine.

2. The compound of claim 1 wherein $R_1$ and $R_2$ are chlorine.

3. The compound of claim 1 wherein $R_1$ is bromine and $R_2$ is hydrogen.

4. An antidepressive composition comprising an effective amount of a compound as defined in claim 1 and a carrier therefor.

5. A method of treatment which comprises administering to a patient suffering depression an effectively anti-depressive amount of a compound defined in claim 1.

* * * * *